United States Patent
Langley et al.

(10) Patent No.: US 7,081,108 B2
(45) Date of Patent: Jul. 25, 2006

(54) PEN-TYPE INJECTOR HAVING HOLDING MECHANISM FOR MEDICAMENT CARTRIDGE

(75) Inventors: Christopher Nigel Langley, Leamington Spa (GB); Shane Alistair Day, Warwick (GB); Robert Frederick Veasey, Leamington Spa (GB); Robert Woolston, Warwick (GB)

(73) Assignee: DCA Design International Limited, Warwick (GB)

( * ) Notice: Subject to any disclaimer, the term of this patent is extended or adjusted under 35 U.S.C. 154(b) by 0 days.

(21) Appl. No.: 10/433,822

(22) PCT Filed: Dec. 21, 2001

(86) PCT No.: PCT/GB01/05726

§ 371 (c)(1),
(2), (4) Date: Jun. 6, 2003

(87) PCT Pub. No.: WO02/051481

PCT Pub. Date: Jul. 4, 2002

(65) Prior Publication Data

US 2004/0044317 A1    Mar. 4, 2004

(30) Foreign Application Priority Data

Dec. 22, 2000 (GB) ................................. 0031466.6

(51) Int. Cl.
    *A61M 5/00*    (2006.01)
(52) U.S. Cl. ...................................... 604/232; 604/234

(58) Field of Classification Search ................ 604/232, 604/234, 235, 243, 151, 187, 263, 240, 250; 600/576–577; 128/912
See application file for complete search history.

(56) References Cited

U.S. PATENT DOCUMENTS

| 3,964,139 | A |   | 6/1976 | Kleinmann et al. |
|-----------|---|---|--------|------------------|
| 5,078,698 | A |   | 1/1992 | Stiehl et al.    |
| 5,423,752 | A |   | 6/1995 | Haber et al.     |
| 5,755,673 | A | * | 5/1998 | Kinsey ............... 600/577 |
| 6,042,571 | A |   | 3/2000 | Hjertman et al.  |

FOREIGN PATENT DOCUMENTS

| EP | 0 362 484 A2 | 4/1990 |
| EP | 0 897 728 A1 | 2/1999 |
| EP | 1 095 668 A1 | 5/2001 |
| GB | 1 467 767    | 3/1977 |
| WO | WO 00/74752 A1 | 12/2000 |

* cited by examiner

*Primary Examiner*—Catherine S. Williams
(74) *Attorney, Agent, or Firm*—Oliff & Berridge, PLC

(57) ABSTRACT

An injection device for injection of a medicament from a medicament cartridge 40 having a neck portion is disclosed. The injection device further comprises a main housing 4 in which the medicament cartridge 40 is releasably retained by first and second retaining means 92,94. The retaining means 92,94 are each moveable between a first position in which the neck portion is engaged thereby to retain the medicament cartridge 40 in the main housing 4 and a second position which allows the medicament cartridge 40 to be removed from the main housing 4.

6 Claims, 5 Drawing Sheets

PEN-TYPE INJECTOR HAVING HOLDING MECHANISM FOR MEDICAMENT CARTRIDGE

The present invention relates to improvements in an injection device, and in particular to improvements in a portable injection device for dispensing controlled quantities of a medicament.

Typically such injection devices are used by those suffering from diabetes to administer a dose of insulin or insulin-type medicine to themselves. It will be understood that such injection devices are suitable for the injection of other medicines.

At one time, such doses were administered by use of a disposable syringe; the syringe first being filled from a separate phial or other container and then used to inject the dose. However, there were a number of difficulties in such an arrangement. In particular, such an arrangement was not suitable for the infirm. For others, the social stigma associated with such syringes made their public use problematic.

To overcome these difficulties a number of so-called pen-type injectors have been developed. These devices are small, being capable of being carried in a jacket pocket or the like and allow a number of doses to be obtained from a cartridge or ampoule contained within the injector. The present invention has particular application to such pen-type injectors.

While such pen-type injectors are a considerable improvement upon disposable hypodermic syringes, problems nevertheless remain.

The present invention provides for improved ease of use and improved interaction with a user.

The invention will now be described, by way of example only, with reference to the accompanying drawings; in which.

Figure 1:
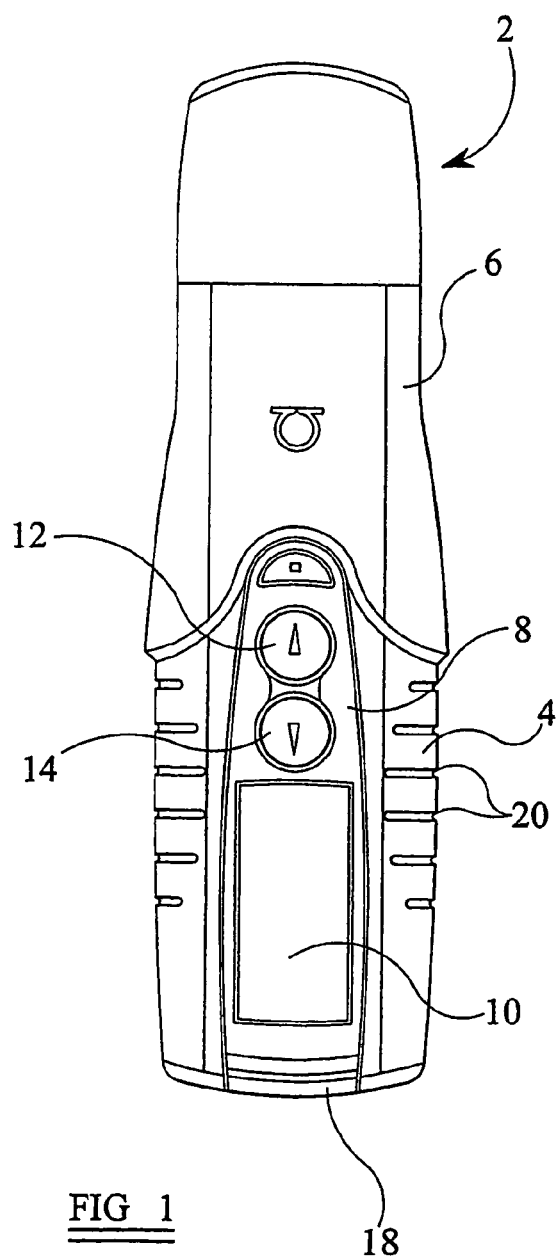
FIG. 1 shows a plan view of a pen-type injector in accordance with the present invention.
Figure 2:
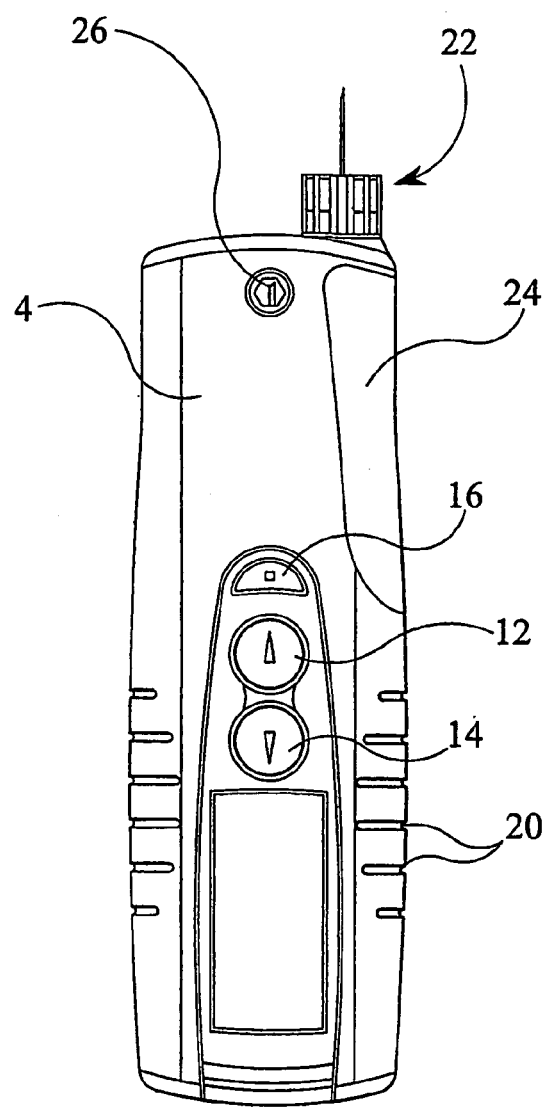
FIG. 2 shows a similar view to FIG. 1 with an end cap of the injector omitted.
Figure 3:
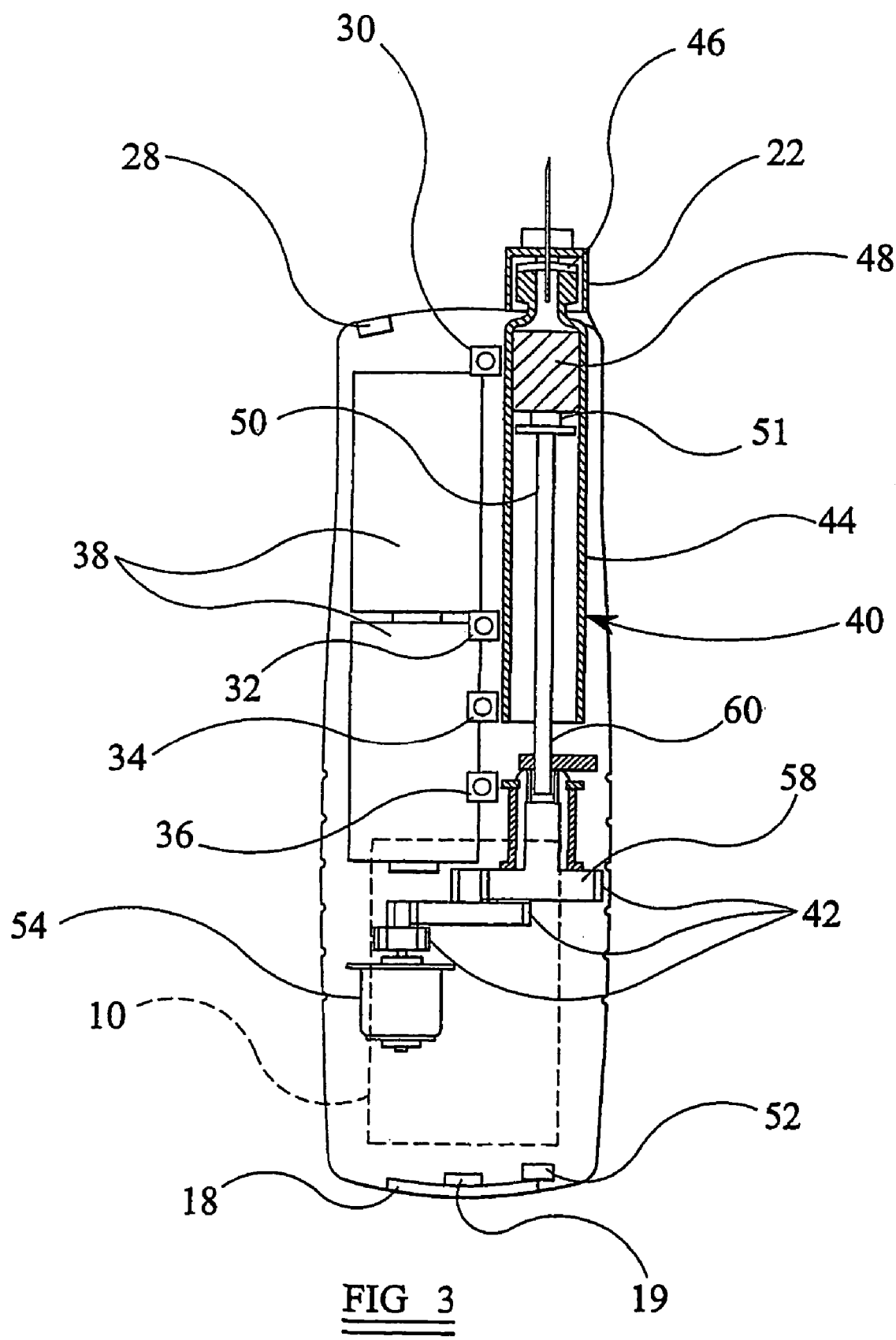
FIG. 3 shows a cross-sectional view of the injector of FIGS. 1 and 2.
Figure 4:
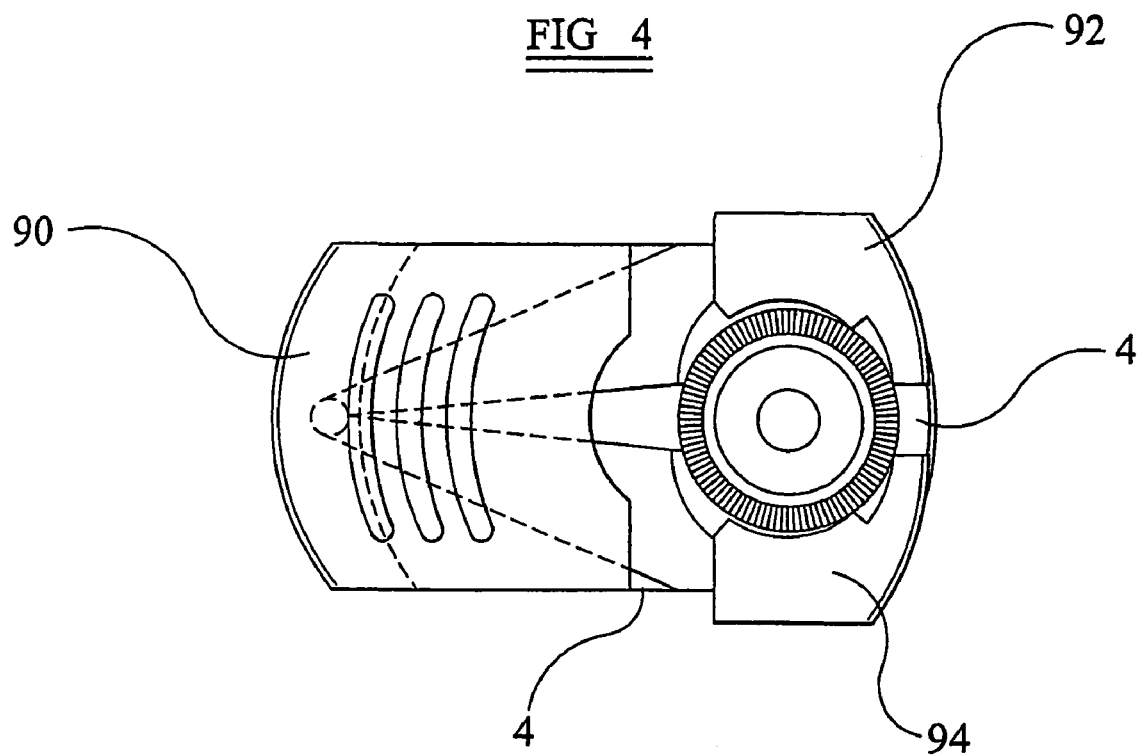
FIG. 4 shows an end view of a further injector in accordance with the present invention with a cover in an open position to allow extraction of a cartridge.
Figure 5:
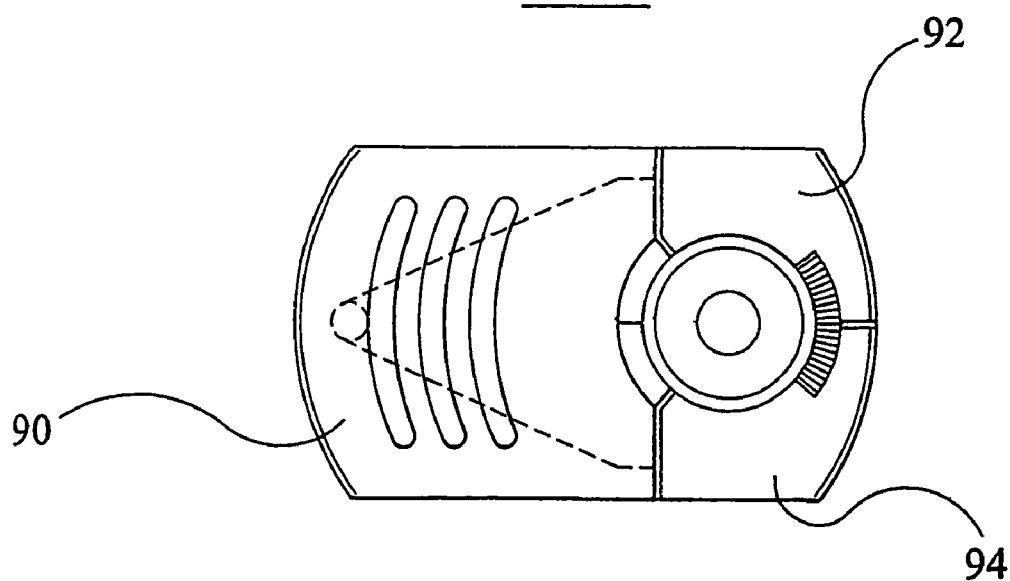
FIG. 5 shows a similar view to FIG. 4 with the cover closed.

Referring first to FIGS. 1 to 3, there can be seen a pen-type injector 2 in accordance with the present invention. The injector 2 comprises a main housing 4 to which is releasably secured an end cap or cover 6.

At the first end of the main housing 4 there is provided a control panel region 8. This region includes a display panel 10, typically a LCD display, and a first dose button 12 and a second dose button 14, the first and second dose buttons being operated to increase or decrease a dose of medicament to be delivered. The control panel region 10 in the illustrated embodiment also includes an arm button 16.

At the first end of the main housing there is also provided a dispense button 18. Preferably, when not depressed, the dispense button 18 is flush with the main housing 4.

Along a longitudinal axis of the injector 2, to each side of the control panel region 10 are provided a number of grooves or recesses 20. These aid in the gripping of the injector 2 by a user.

At a second end of the main housing 4 a needle unit 22 is releasably secured to the main housing. The second end of the main housing 4 is also provided with a shaped portion 24.

In use a cartridge 40 or ampoule of medicament is stored in the housing 4 behind the shaped portion 24. For preference, the shaped portion is transparent to permit the cartridge 40 to be seen by a user.

A primer button 26 is also provided on the second end of the housing 4. It will be understood that when the end cap 6 is in place over the second end of the housing, it will not be possible inadvertently to depress the primer button 26 or to be pricked by the needle unit 22. A cover detection switch 28 may also be included at the second end of the main housing 4 to detect whether the end cap or cover 6 is in place or not.

In FIG. 3, there can be seen a priming contact 30, an arm contact 32, a first dose contact 34 and a second dose contact 36 corresponding to the respective buttons. A dispense contact 19 corresponding to the dispense button 18 is also shown.

With reference to FIG. 3 it may be seen that there is provided a suitable location for a power source 38 such as a battery or batteries. There is also a suitable region in which a cartridge 40 or ampoule of medicament is to be located. This region may be accessed by way of the removable shaped portion 24 of the main housing 4 to allow for replacement of the cartridge 40 or ampoule as required by the user. An alternative cartridge access means is disclosed in relation to FIGS. 4 to 9.

In a third region of the main housing 4 there is provided a drive mechanism 42 which operates from the power source 38 and acts upon the cartridge 40 or ampoule of medicament.

The cartridge 40 or ampoule comprises a container 44 or sleeve closed at one end by a cover 46 at a head end thereof, and sealed at the other by a movable bung 48 or stopper. When in position, the needle unit 22 pierces the cover 46 and movement of the bung 48 towards the cover 46 will cause the medicament contained within the cartridge 40 or ampoule to be expelled. The cartridge may be a 3 ml cartridge in accordance with ISO/FDIS 11608 Part 3, or any other suitable cartridge to suit the injector.

Movement of the bung 48 or stopper is caused by movement of a piston or plunger 50 forming a part of the drive mechanism 42. The piston or plunger 50 is movable between a first fully withdrawn position (not shown) which allows for the replacement of the cartridge 40 or ampoule and a second fully extended portion in which as much medicament as possible has been expelled from the cartridge 40 or ampoule. An end stop switch 52 may be provided in the main housing 4 to detect when the piston 50 is in the fully withdrawn position. Tripping of the switch end stop 52 may release a catch or other fastening device to allow access to the main housing 4 for replacement of the cartridge 40.

The drive mechanism 42 is operated by a motor 54 under the control of an electronic control unit (not shown). The motor 54 should be reversible in order to allow the piston 50 to be moved between the first and second positions. In FIG. 3, the motor 54 can be seen to drive the piston 50 by way of a gear train 42, such that rotation of a third rotor 58 causes the piston 50 to be moved in relation to the third rotor 58.

Preferably, the user can feel the vibration of the motor 54 and the associated drive mechanism 42 and/or hear them in operation. In this way an added degree of confidence in the fact of the operation of the injector 2 is provided to the user.

The control buttons have a number of functions. The dose buttons 12,14 allow a user to select a desired dosage. The dose arm button 16 allows a user to confirm selection of a desired dosage. The first dose button can increment the dosage level and the second dose button can decrement the dosage level. The dose dialling buttons 12,14 may be pressed down (and held for a short time, 1–2 seconds) to re-set a dose value to zero. The user can then dial up (or down) in single (or half) increments.

The dose dialling buttons 12,14 are intended to be pressed once for a single (or half) increment in the selected dose value. In an alternative embodiment, pressing and holding one of the buttons will cause the dose value to start to scroll (up or down) in order to change the dose size more rapidly.

The dispense button 18 allows a user to initiate dispensing of the dosage. The primer button 26 dispenses a unit of dosage from the cartridge 40. Thus, if any air is trapped in the injector 2 this can be expelled by use of the primer button 26. A door release catch is provided to allow access to the cartridge 40.

Since the cartridge 40 is of a standard size, each cartridge 40 will be emptied by an identical travel of the plunger driven by the drive mechanism. Once the plunger 50 is in the fully extended position, the cartridge 40 is known to be empty and an indication of this will be provided to the user.

When the door release catch is operated for the emptied cartridge 40 to be removed the drive mechanism 42 is operated to reverse a lead screw 60 to withdraw the plunger 50 until the lead screw 60 strikes the end stop switch 52 which is provided at a known reference point.

When a new cartridge 40 is detected, for example by way of a contact switch (not shown), and the door release catch closed, the electronic control unit advances the lead screw 60 until the plunger 50 strikes the cartridge bung 48. This may conveniently be done by fitting a micro-switch 51, such as a dome contact switch to a free end of the plunger 50.

Since the exact position of the bung 48 can be calculated with reference to the rear end stop 52, a number of units of medicament stored within the cartridge 40 can be determined. Thus a half empty or incorrectly filled cartridge 40 may be used with the injector 2 of the present invention. The electronic control unit having determined the number of units stored within the cartridge preferably will not allow a dosage larger than that remaining to be dialled up for dispense.

Figure 6:
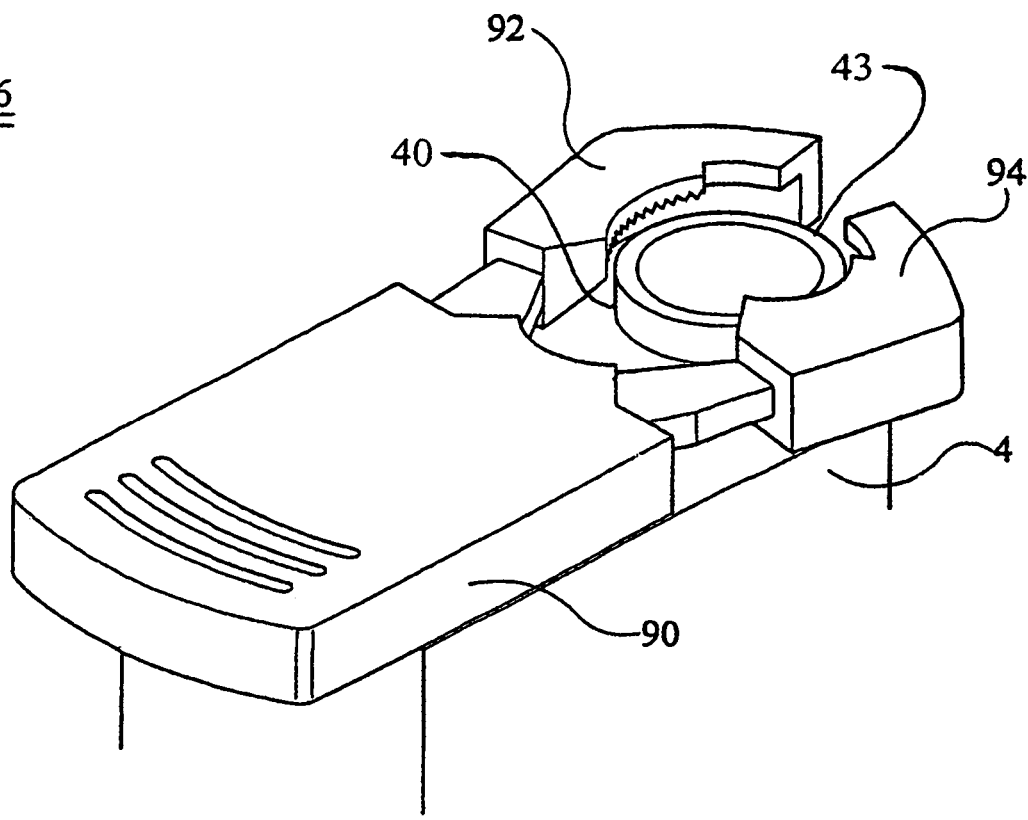
FIG. 6 shows a perspective view of the cover of FIGS. 4 and 5 in an open position.

In the embodiment of FIGS. 4 to 9, there can be seen a tab 90. The tab 90 is constrained for sliding movement within or on the main housing 4. As seen in FIG. 6, the tab 90 is adapted to slide in grooves 91 provided on the main housing 4. When the tab 90 is withdrawn a slider mechanism (FIGS. 5 to 9) causes first and second jaws 92, 94 to move radially outwardly from a neck of the cartridge 40 or adaptor 43 to allow removal of the cartridge 40.

Figure 7:
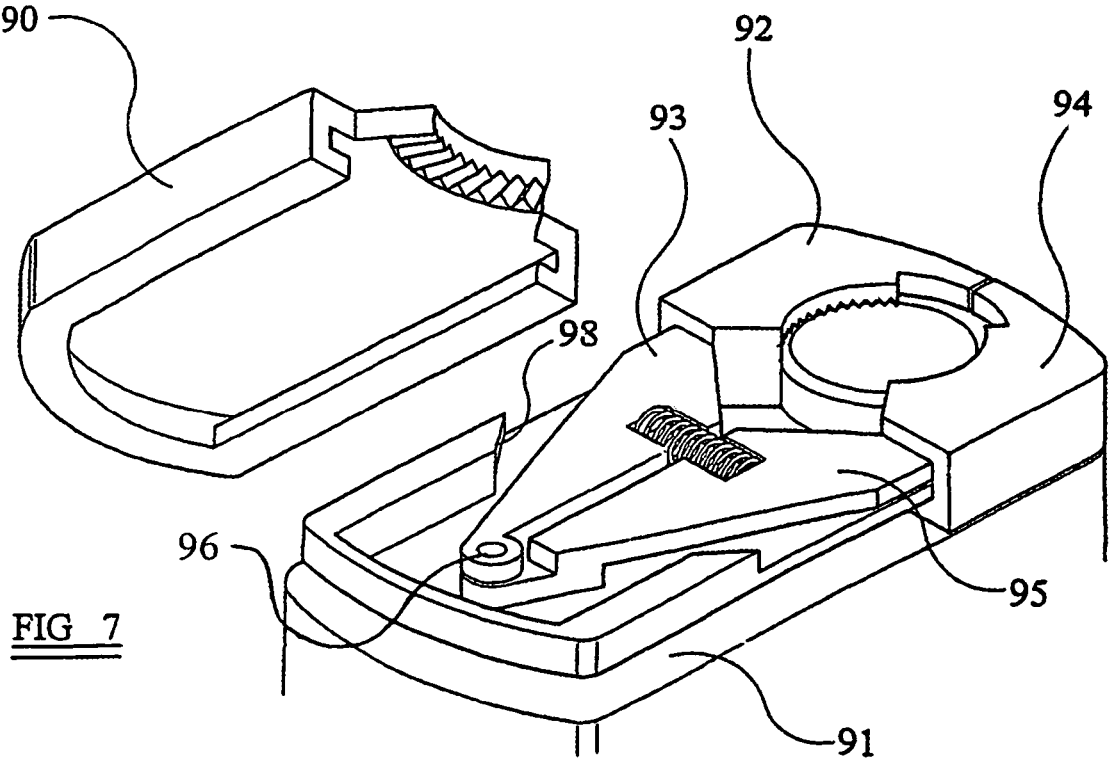
FIG. 7 shows details of the cover illustrated in FIG. 6.
Figure 8:
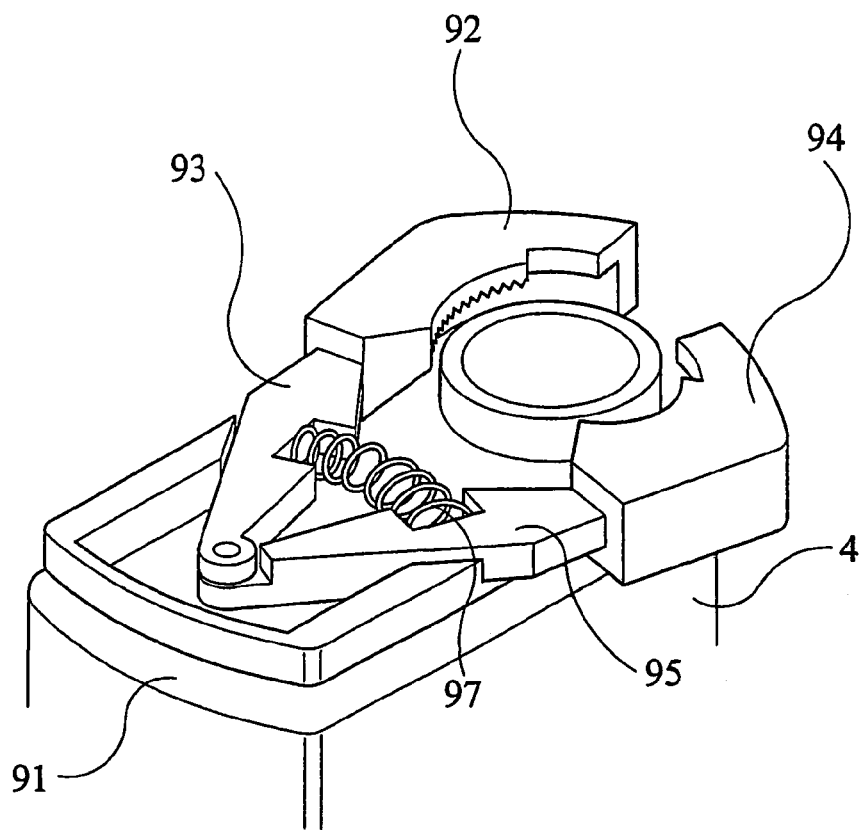
FIG. 8 shows the opening mechanism shown in FIG. 7 in an open position.
Figure 9:
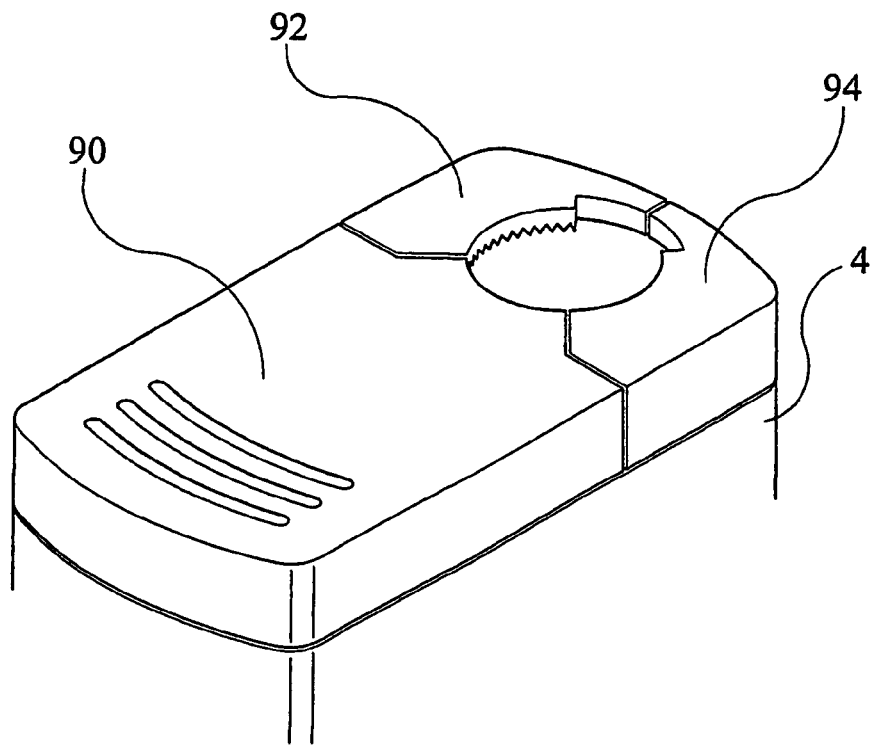
FIG. 9 shows a view similar to FIG. 6 with the cover closed.

The slider mechanism can be seen most clearly in FIGS. 6 and 7. The first and second jaws 92, 94 are each disposed on respective elongate arms 93, 95. The arms are adapted to pivot about at point 96 located at ends remote from the jaws 92,94. Spring means 97 is provided between the arms 93, 95 to bias the arms away from one another. The slider mechanism is located within a recess formed in the main housing 4. The recess is conveniently provided with walls 98 which act as end stops to limit the travel of the arms 93,95. Thus once the tab 90 begins to move it is aided by the arms 93,95 separating under the action of the spring means 97 until the arms abut the walls 98.

Sliding the tab 90 home conversely pushes the arms 93,95 together against the action of the spring means 98 and causes the jaws 92, 94 to lock about the cartridge 40 or the adaptor 43 as required. Latching means are provided to retain the tab 90 in the closed position.

The invention claimed is:

1. An injection device for injection of a medicament from a medicament cartridge having a neck portion, the injection device comprising:
   a main housing in which the medicament cartridge is releasably retained by first and second retaining means, the retaining means each being moveable between a first position in which the neck portion is engaged thereby to retain the medicament cartridge in the main housing and a second position which allows the medicament cartridge to be removed from the main housing;
   spring means disposed between the first and second retaining means to urge the first and second retaining means toward the second position; and
   a slider tab acting on each of the first and second retaining means to urge the first and second retaining means towards the first position.

2. An injection device according to claim 1, wherein, the slider tab acts on an external face of each of the first and second retaining means.

3. An injection device according to claim 1, wherein, the slider tab is slidably retained within a groove formed in the main housing.

4. An injection device according to claim 1, wherein, the slider tab is adapted to engage the neck portion of the medicament cartridge.

5. An injection device according to claim 1, wherein, the main housing includes an end stop to prevent movement of the first and second retaining means beyond the second position.

6. An injection device according to claim 1, wherein, the first and second retaining means move radially about a common pivot point.

* * * * *